US009121915B2

(12) United States Patent
Wu et al.

(10) Patent No.: US 9,121,915 B2
(45) Date of Patent: Sep. 1, 2015

(54) MULTI-DIMENSIONAL CARDIAC AND RESPIRATORY IMAGING WITH MRI

(75) Inventors: Holden H Wu, Mountain View, CA (US); Bob S Hu, Los Altos, CA (US)

(73) Assignees: The Board of Trustees of the Leland Stanford Junior University, Palo Alto, CA (US); Palo Alto Medical Foundation for Healthcare, Research and Education, Palo Alto, CA (US)

( * ) Notice: Subject to any disclaimer, the term of this patent is extended or adjusted under 35 U.S.C. 154(b) by 792 days.

(21) Appl. No.: 13/374,045

(22) Filed: Dec. 8, 2011

(65) Prior Publication Data

US 2012/0146641 A1 Jun. 14, 2012

Related U.S. Application Data

(60) Provisional application No. 61/459,238, filed on Dec. 9, 2010.

(51) Int. Cl.
| | |
|---|---|
| A61B 5/055 | (2006.01) |
| G01R 33/48 | (2006.01) |
| A61B 5/05 | (2006.01) |
| A61B 6/00 | (2006.01) |
| G01R 33/56 | (2006.01) |
| G01R 33/563 | (2006.01) |
| G01R 33/567 | (2006.01) |

(52) U.S. Cl.
CPC .............. *G01R 33/4826* (2013.01); *A61B 5/05* (2013.01); *A61B 6/503* (2013.01); *G01R 33/5602* (2013.01); *G01R 33/5635* (2013.01); *G01R 33/5673* (2013.01); *G01R 33/56341* (2013.01); *G01R 33/56366* (2013.01)

(58) Field of Classification Search
USPC ......................... 324/300–322; 600/407–437; 382/128–131
See application file for complete search history.

(56) References Cited

U.S. PATENT DOCUMENTS

| | | | | |
|---|---|---|---|---|
| 8,781,197 | B2 * | 7/2014 | Wang et al. | 382/131 |
| 2007/0032733 | A1 * | 2/2007 | Burton | 600/509 |
| 2011/0044524 | A1 * | 2/2011 | Wang et al. | 382/131 |
| 2011/0215805 | A1 * | 9/2011 | Doyle | 324/309 |
| 2012/0078083 | A1 * | 3/2012 | McConnell et al. | 600/413 |
| 2012/0146641 | A1 * | 6/2012 | Wu et al. | 324/309 |

* cited by examiner

*Primary Examiner* — Melissa Koval
*Assistant Examiner* — Tiffany Fetzner
(74) *Attorney, Agent, or Firm* — Lumen Patent Firm

(57) ABSTRACT

A 5-dimensional imaging method and system is provided to acquire and display the effect of dynamic physiologic changes (either spontaneous or induced) on cardiac function of a patient's heart to elucidate their effects on diastolic myocardial function. In a patient free-breathing magnetic resonance imaging study, 3-dimensional spatial information is encoded by a non-Cartesian 3-dimensional k-space readout trajectory and acquired concurrently with recordings of cardiac and respiratory cycles. The advantage of using non-Cartesian sampling in this invention compared to, for example, Cartesian sampling is higher scan acceleration, improved robustness to motion/flow effects (incoherent instead of coherent artifacts) and robustness to missing data points in k-space.

13 Claims, 5 Drawing Sheets

MULTI-DIMENSIONAL CARDIAC AND RESPIRATORY IMAGING WITH MRI

CROSS-REFERENCE TO RELATED APPLICATIONS

This application claims priority from U.S. Provisional Patent Application 61/459,238 filed Dec. 9, 2010, which is incorporated herein by reference in its entirety.

STATEMENT OF GOVERNMENT SPONSORED SUPPORT

This invention was made with Government support under contracts R01-HL039297 and NIH/NIBIB T32-EB009035 awarded by National Institutes of Health (NIH). The Government has certain rights in this invention.

FIELD OF THE INVENTION

The invention relates to multi-dimensional cardiac imaging methods and systems.

BACKGROUND OF THE INVENTION

Diastolic left ventricular (LV) dysfunction remains one of the most important cardiac diseases for which current noninvasive diagnostic techniques remain inadequate. For instance, more than 60% of women admitted for congestive heart failure have diastolic dysfunction as the cause of their symptoms. However, current noninvasive diagnostic criteria (primarily utilizing echocardiography) are able to reliably classify only 60-70% of the patients.

Central to the idea of diastolic dysfunction is the alteration of the pressure-volume relationship of the left ventricle. This relationship is best evaluated under dynamic changes in the ventricular loading condition e.g. while the patient is breathing.

Fast magnetic resonance imaging (MRI) techniques have enabled the acquisition of volumetric datasets within a patient-tolerable examination time. However, many patient datasets are "corrupted" by dynamic physiologic motion. Much of the research in volumetric data acquisition has been aimed at removing these dynamic effects. The present invention takes a different approach and provides a method and system to acquire and display the effect of these dynamic physiologic changes (either spontaneous or induced) on cardiac function to elucidate their effects on diastolic myocardial function.

SUMMARY OF THE INVENTION

The present invention provides a 5-dimensional imaging method and system to acquire and display the effect of dynamic physiologic changes (either spontaneous or induced) on cardiac function of a patient's heart to elucidate their effects on diastolic myocardial function: In a patient free-breathing magnetic resonance imaging study of said patient's heart, a computer system is used to acquire 3-dimensional spatial information and concurrently acquires recordings of cardiac and respiratory cycles of the patient. The 3-dimensional spatial information is sampled with a non-Cartesian 3-dimensional k-space readout trajectory which is incorporated into a magnetic resonance imaging sequence. The magnetic resonance imaging sequence could utilize principles of free-induction decay, steady-state free precession, gradient echo, spin echo, magnetization preparation modules, or a combination thereof to prepare image contrast from the magnetic resonant spins. The non-Cartesian 3-dimensional k-space readout trajectory traverses data points along arbitrary trajectories instead of straight rectilinear line trajectories common in Cartesian sampling. Examples of traversing data points could be along intersecting diagonal line trajectories, spiraling trajectories, circular trajectories in 3D k-space, or a combination thereof. Compared to traditional rectilinear Cartesian sampling, the non-Cartesian sampling provides higher scan acceleration (e.g., 3- to 8-fold or higher), improves robustness to motion/flow effects (incoherent instead of coherent artifacts) and provides robustness to missing data points in k-space.

The acquisition typically includes a plurality of segments of a plurality of readouts and each segment is repeated multiple times to cover at least a full period of a cardiac and respiratory cycle of the patient. All segments are acquired to cover the full set of readouts. For each cardiac and respiratory temporal phase combination in the recorded cycles, the computer system further calculates and displays 3-dimensional volumetric measurements of the atria and ventricles of the patient's heart and the rate of change of these measured volumes with respect to the cardiac and respiratory cycles.

The non-Cartesian 3-dimensional k-space readout trajectory could be a non-Cartesian 3-dimensional cones k-space readout trajectory, a non-Cartesian 3-dimensional echo-planar imaging (EPI) k-space readout trajectory, non-Cartesian 3D Periodically Rotated Overlapping ParallEL Lines with Enhanced Reconstruction (PROPELLER) k-space readout trajectory, non-Cartesian 3D stack of spirals k-space readout trajectory, non-Cartesian 3D stack of rings k-space readout trajectory, or a non-Cartesian 3-dimensional projection reconstruction (PR) k-space readout trajectory, or other rapid 3D k-space readout trajectory.

In one embodiment the acquisition of 3-dimensional spatial information is enhanced with MRI acceleration techniques including, but not limited to, parallel imaging, spatiotemporal undersampling and reconstruction, or compressed sensing.

In another embodiment, the 3-dimensional spatial information and respiratory and cardiac information could be complemented with flow information, perfusion information or a combination thereof.

In still another embodiment, the 3-dimensional spatial information and respiratory and cardiac information could be complemented with MRI T1-relaxation information, MRI T2-relaxation information, or a combination thereof.

In still another embodiment, the 3-dimensional spatial information and respiratory and cardiac information could be complemented with oxygenation level information, the distribution of an administered contrast agent or a combination thereof.

In yet another embodiment, the study could further include internally or externally induced respiratory pressure variations to the patient.

DETAILED DESCRIPTION

A 5-dimensional (5D) representation of the heart, including 3D spatial information, 1D cardiac phase information, and 1D respiratory phase information, is acquired during a free-breathing magnetic resonance imaging (MRI) study. Additional dimensions of information, such as perfusion or flow, can augment this 5D acquisition.

Data Acquisition

Figure 1:
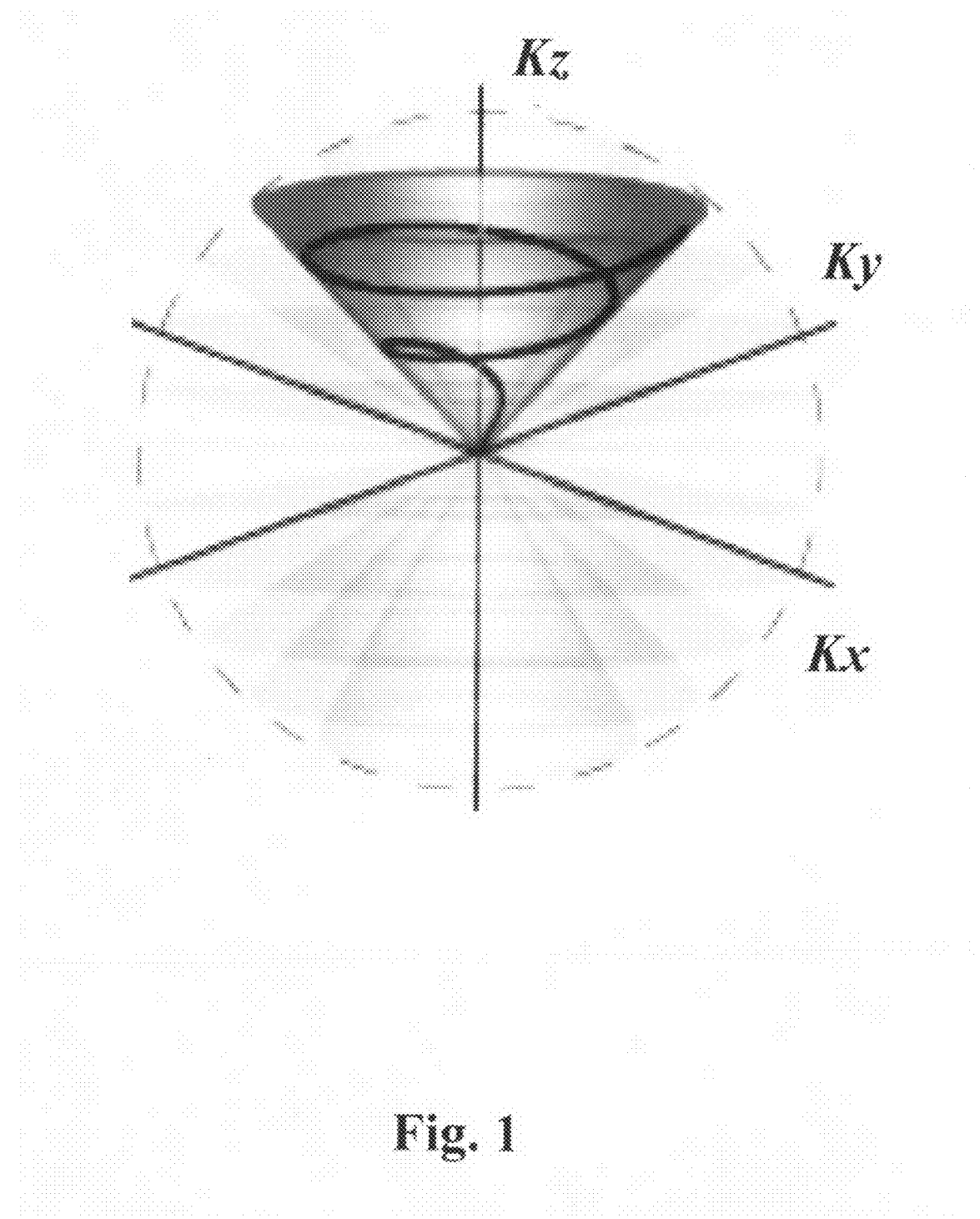
FIG. 1 shows a 3D cones k-space trajectory according to an exemplary embodiment of the invention.

1. A non-Cartesian 3D cones k-space readout trajectory is used to acquire volumetric MRI data (FIG. 1). The desired spatial field of view (FOV) and spatial resolution are used to calculate the 3D cones trajectory. Compared to traditional rectilinear Cartesian sampling, the 3D cones provide scan acceleration (3- to 8-fold or higher), improve robustness to motion/flow effects (incoherent instead of coherent artifacts) and provide robustness to missing data points in k-space.

In Cartesian sampling the desired data points in k-space correspond directly to a rectilinear Cartesian grid, with data points acquired along a single straight line in k-space after each MR signal excitation and the full set of data points acquired with multiple lines (excitations). In non-Cartesian sampling data points in k-space are not constrained to a rectilinear Cartesian grid, with data points acquired along arbitrary paths/trajectories in k-space after each MR signal excitation and the full set of data points acquired with multiple arbitrary paths (excitations). As more k-space data points can be acquired along an arbitrary trajectory (e.g., a circular or spiraling path), fewer excitations are required and overall scan time is reduced compared to acquisition with only straight Cartesian lines. Non-Cartesian sampling also avoids coherent ghosting artifacts in the reconstructed image when data points are missing (seen in Cartesian sampling). Furthermore, non-Cartesian trajectories can be designed to take advantage of the varying signal characteristics in k-space and improve MR image quality through enhancement of contrast or minimization of motion/flow effects.]

Figure 2:
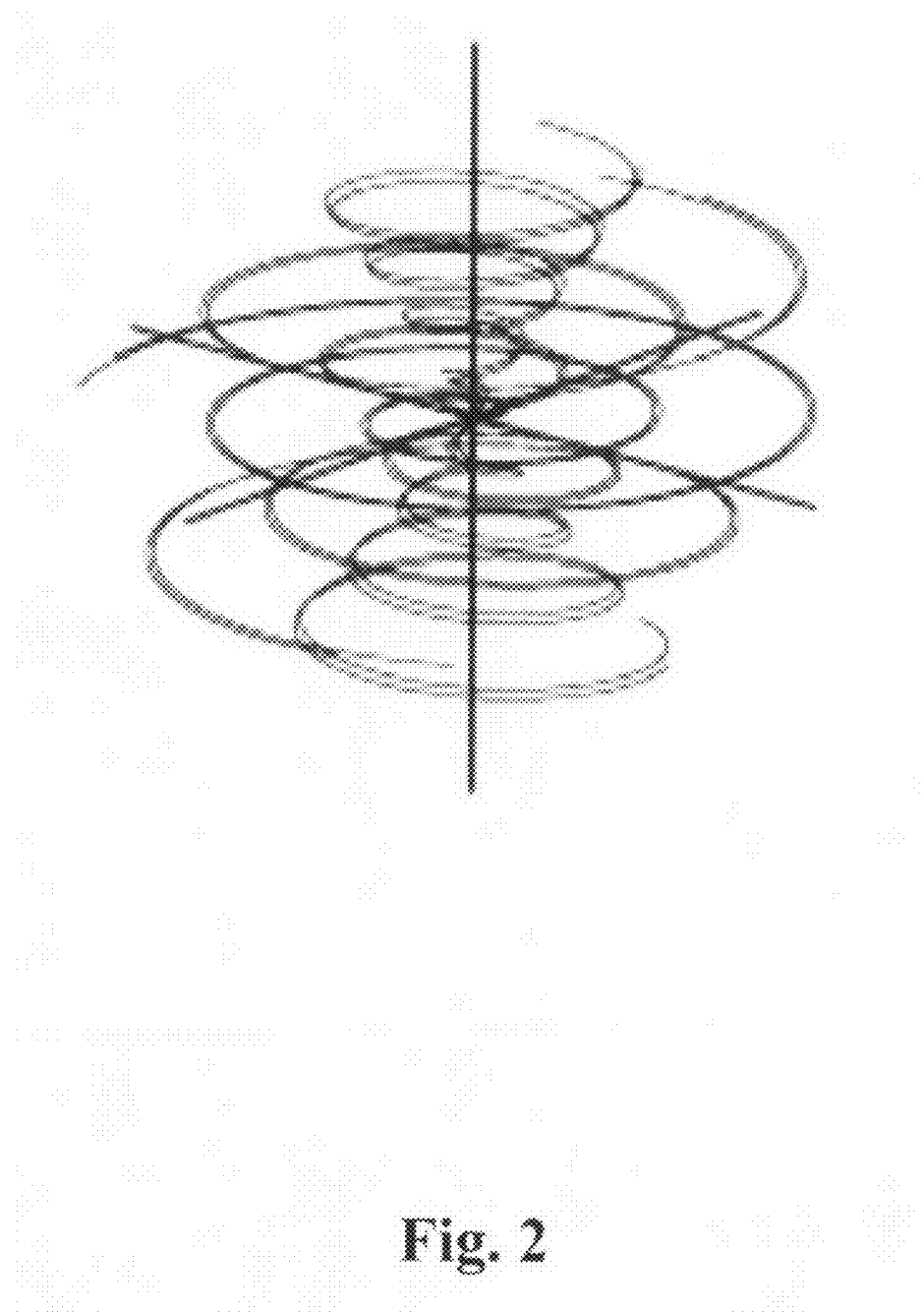
FIG. 2 shows a sample interleaved k-space acquisition segment including 10 cone readouts. Note the pairing of adjacent readouts according to an exemplary embodiment of the invention.
Figure 3:
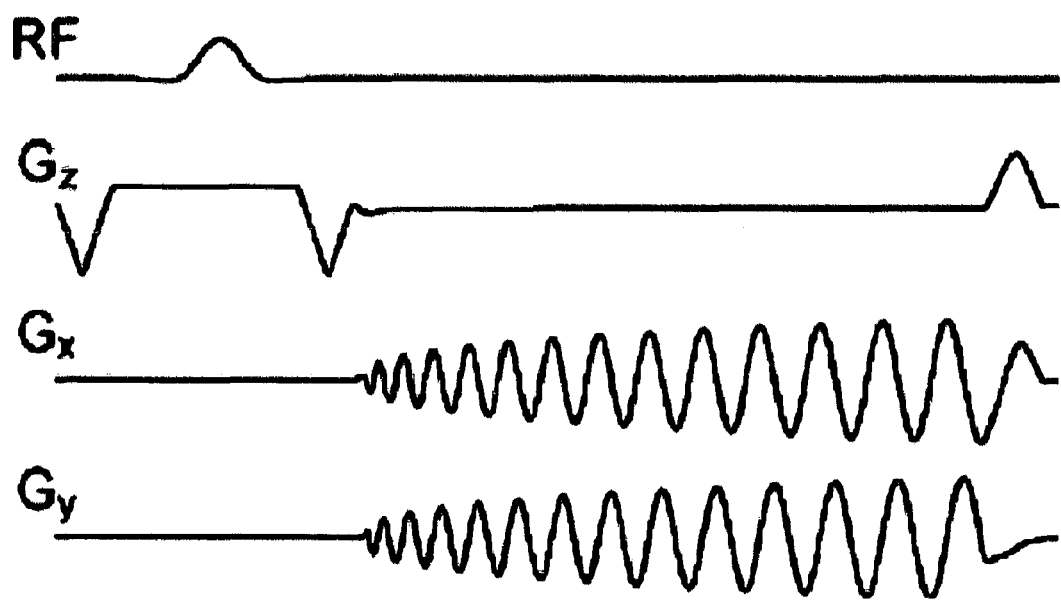
FIG. 3 shows a steady-state free precession (SSFP) cones imaging sequence according to an exemplary embodiment of the invention.

2. The 3D cones k-space trajectory is incorporated into a steady-state free precession (SSFP) imaging sequence (FIG. 3). The full set of 3D cone readouts (e.g., 300 readouts) is organized into several segments (e.g., 10 readouts/segment and 30 segments) and acquired over multiple cardiac and respiratory cycles (FIG. 2). Segmentation can be either sequential or interleaved and improves the temporal resolution of the acquisition. Pairing or grouping of readouts may be done for each segment to mitigate eddy current artifacts. Each segment is acquired multiple times to cover at least one full period of the cardiac and respiratory cycles before going on to acquire the next segment. This is repeated until all segments (and thus readouts) have been acquired.

Figure 4:
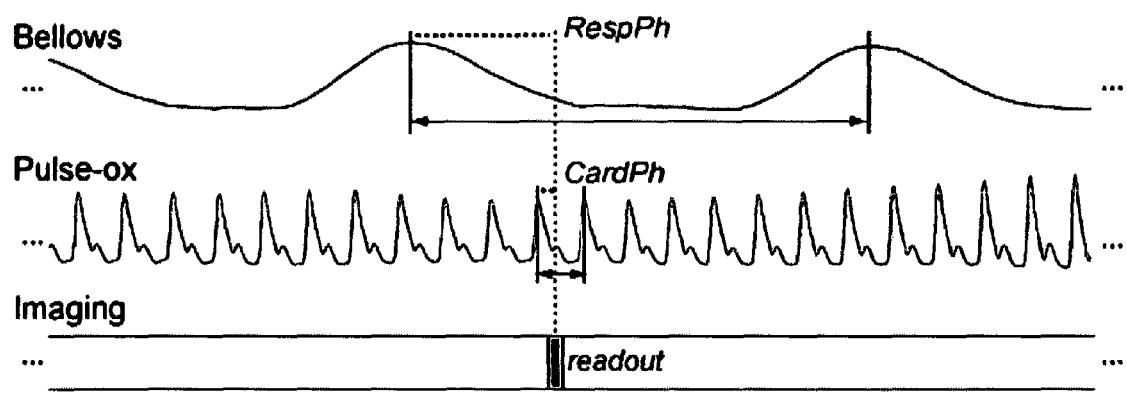
FIG. 4 shows according to an exemplary embodiment of the invention the respiratory phase (RespPh) and cardiac phase (CardPh) of each readout which are retrospectively determined from the recorded physiologic signals (e.g., bellows for respiratory, motion and pulse-ox plethysmograph for cardiac motion). Acquired data are then re-ordered and reconstructed to obtain a 5D matrix.

3. Data acquisition is performed continuously throughout a scan and not prospectively gated to any physiologic signal. Physiologic signals (e.g., electrocardiogram (ECG), pulse-oximeter plethysmograph, respiratory bellows, navigators, or self-navigation information, etc.) are monitored and recorded concurrently for retrospective data re-ordering (FIG. 4).

Data Reconstruction

4. After concluding data acquisition, the physiologic signals are synchronized to the imaging readouts (e.g., via timestamps) and used to determine the cardiac phase (CardPh) and respiratory phase (RespPh) of each readout. This can be accomplished, for example, by looking at the relative temporal position of a readout in the local cardiac and respiratory cycles (FIG. 4).

5. The number of cardiac phases ($N_{CardPh}$) and respiratory phases ($N_{RespPh}$) to reconstruct is determined. For example, $N_{RespPh} = (T_{RespAvg}/T_{CardAvg})$ and $N_{CardPh} = (T_{CardAvg}/T_{Seg})$, where $T_{RespAvg}$ is the average respiratory cycle duration, $T_{CardAvg}$ is the average cardiac cycle duration, and $T_{Seg}$ is the duration of one acquisition segment.

6. Data is then re-ordered into a 5D data matrix. Repeated acquisitions of the same entry in this matrix could be averaged. Missing data entries are estimated from neighboring points, where the last/first phases are considered neighbors (assuming periodic motion). Estimation can be simple nearest-neighbor interpolation or more sophisticated multipoint spatiotemporal interpolation.

7. For each (CardPh, RespPh) combination, a volume is reconstructed by 3D re-gridding followed by a regular 3D Fourier transform. Data from multiple receiver channels are combined (e.g., using a root of sum of squares).

Data Analysis and Display

8. Volume measurements of the atria and ventricles and the rate of change of these volumes could be performed manually, semi-automatically, or automatically, and plotted with respect to the cardiac and/or respiratory cycles.

Variations and/or Other Embodiments

Multiple rapid MRI acquisition strategies could be used in combination to sample the multiple dimensions of anatomic and physiologic information, including advanced time-efficient non-rectilinear sampling methods (e.g. 3D cones, 3D stack-of-rings), motion-robust and contrast-enhancing acquisition scheduling, parallel imaging acceleration, spatiotemporal undersampling acceleration (e.g. k-t BLAST), compressed sensing theory (e.g. robust algorithms to reconstruct from sparse measurements), and other approaches exploiting a priori information.

Automated, semi-automated, or manual determination could be performed of anatomic measurements and functional information from the acquired multi-dimensional dataset. For example, volume measurements of the atria and ventricles as calculated from the 3D morphology and the rate of change of the measured volumes with respect to cardiac and/or respiratory motion.

Integrated visualization of the anatomic, physiologic, and derived measurements is established. This includes, but is not limited to, volume/surface rendering of the 3D morphology displayed as a temporal sequence with respect to cardiac and/or respiratory motion, plotting the derived measurements with respect to cardiac and/or respiratory motion, and perfusion and flow measurements overlaid on the 3D temporal sequence.

Tests based on the described technique could be performed where external or internal agents can be activated to alter the physiologic state of the subject and the differences are documented and observed. Repeated applications of the technique over a prolonged duration of time can also be performed to characterize inherent variations in the resting physiologic state of the subject.

EXAMPLE

1. General Time-resolved Volumetric Acquisition
Acquisition
  a. Continuous steady-state acquisition.
  b. Use the 3D cones for spatial encoding.
  c. Optional magnetization-preparation modules inserted for encoding of flow, diffusion, chemical shift, or other functional information.
  d. Cardiac and respiratory information concurrently recorded during the scan from standard monitoring devices (ECG, pulse-ox, bellows) and/or MRI navigator signals.
  e. Scan time reduction using multiple receiver elements.
Reconstruction
  a. Retrospective synchronization of acquired anatomic/functional data to physiologic temporal phases (cardiac/respiratory phase).
  b. Reconstruction of an entire volumetric and/or functional dataset for each desired temporal phase.
Processing and Display
  a. Slice-by-slice or volume-rendered display of the 3D morphology as a temporal sequence with respect to cardiac motion at each stage of the respiratory cycle; a plot of the measured atrial/ventricular volumes and rate of change at each temporal phase.
  b. Slice-by-slice or volume-rendered display of the 3D morphology as a temporal sequence with respect to respiratory motion at each stage of the cardiac cycle; a plot of the measured atrial/ventricular volumes and rate of change at each temporal phase.
2. T1-weighted Time-resolved Volumetric Acquisition
Acquisition
  a. Inversion-recovery-prepared gradient-echo acquisition.
  b. Use the 3D stack-of-rings for spatial encoding.
  c. Optional magnetization-preparation modules inserted for encoding of flow, diffusion, chemical shift, or other functional information.
  d. Prospective cardiac triggering for synchronization of inversion recovery modules.
  e. Respiratory information concurrently recorded during the scan from standard bellows and/or MRI navigator signals.
  f. Scan time reduction using multiple receiver elements.
  g. Optional administration of a T1-shortening imaging agent.
  h. Multiple repetitions of such acquisitions with different inversion-recovery delay (TI) values.
Reconstruction
  a. Retrospective synchronization of acquired anatomic/functional data to physiologic temporal phases (cardiac/respiratory phase).
  b. Reconstruction of an entire volumetric and/or functional dataset for each desired physiologic temporal phase.
  c. Derive tissue T1 values based on multiple acquisitions with different TI values.
Processing and Display
  a. Slice-by-slice or volume-rendered display of the 3D morphology as a temporal sequence with respect to cardiac motion at each stage of the respiratory cycle.
  b. Slice-by-slice or volume-rendered display of the 3D morphology as a temporal sequence with respect to respiratory motion at each stage of the cardiac cycle.
  c. Slice-by-slice or volume-rendered display of the contrast distribution as a temporal sequence with respect to the underlying morphology and physiologic phases.
  d. Slice-by-slice or volume-rendered display of the tissue T1 values as a temporal sequence with respect to the underlying morphology and physiologic phases.

Figure 5A:
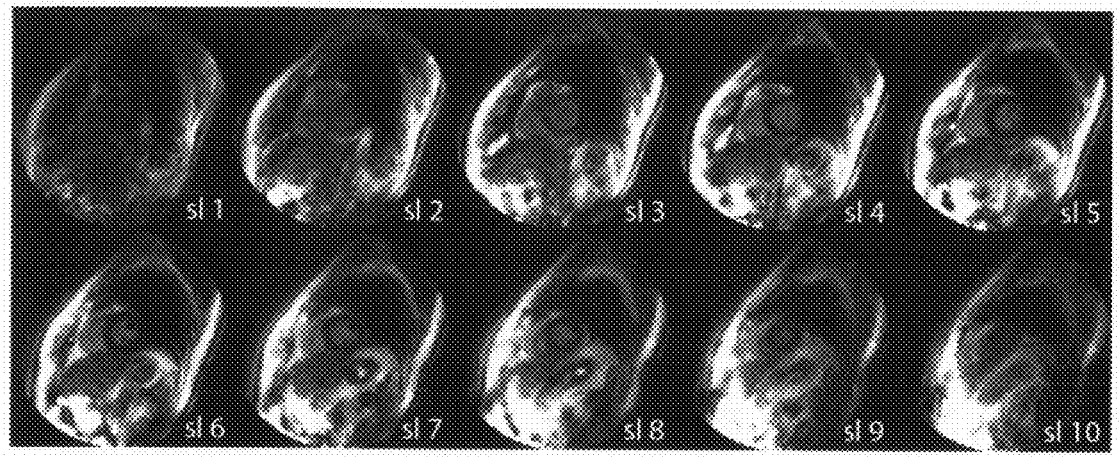
FIGS. 5A-C according to examples of the invention (A) shows 10 slices (sl1-sl10) at end diastole and end expiration from a healthy volunteer acquired during a baseline free-breathing 5D scan (B) shows the first 5 resolved respiratory phases of the central slice at end diastole from a baseline free-breathing 5D scan. (C) shows the first 5 resolved respiratory phases of the matching slice at end diastole during a free-breathing scan modulated with a continuous positive airway pressure (CPAP) device set to 15 cm-H2O. The diaphragm is at a lower position due to increased intra-thoracic pressure and the volume of the left ventricle is reduced.
Figure 5B:
Figure 5C:
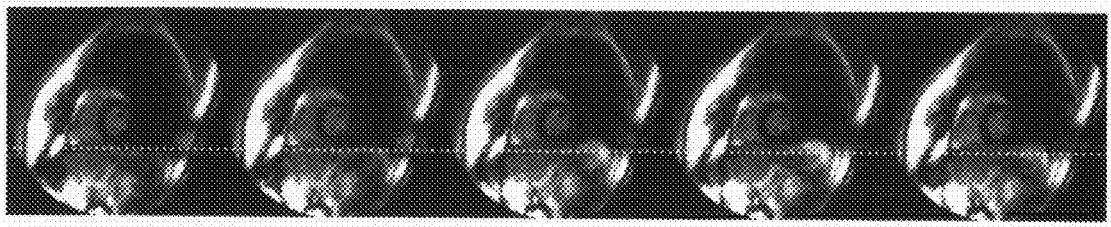

EXEMPLARY RESULTS 1. 5D Cardiac Imaging Using the 3D Cones
Acquisition
  a. Continuous steady-state free precession (SSFP) acquisition.
  b. 3D cones for spatial encoding of a 36×36×8 $cm^3$ FOV and 2.4×2.4×8 $mm^3$ resolution (150×150×10 matrix). 300 readouts acquired at 10 readouts/segment (30 segments).
  c. 50-ms temporal resolution for each acquisition segment. Each segment repeated for 8 s to cover at least one full respiratory cycle.
  d. Respiratory bellows and peripheral pulse-ox plethysmograph recorded concurrently during scan.
  e. Free-breathing scan of 4 min 30 s.
  f. Repeated free-breathing scans using a continuous positive airway pressure (CPAP) device to modulate the intrathoracic pressure.
Reconstruction
  a. Retrospective synchronization of acquired anatomic data to respiratory and cardiac phases.
  b. Reconstruction of entire imaging volume for each desired respiratory and cardiac phase.
Processing and Display
  Display as a temporal sequence of the 3D volume (as 2D slices) with respect to the cardiac and respiratory cycles (FIGS. 5a-c).
2. Volumetric Single-phase T1-weighted Head Imaging Using the 3D Stack-of-rings
Acquisition
  a. Inversion-recovery prepared spoiled gradient-echo acquisition.
  b. 3D stack-of-rings for spatial encoding of a 24×24×18 $cm^3$ FOV and 1×1×1 $mm^3$ resolution.
  c. Three echoes collected for fat/water separation.
  d. 2-fold acceleration using an 8-channel head coil (3 min 30 s scan).
Reconstruction
  a. Reconstruction of volumetric data for the three echoes (8 channels).
  b. Fat/water separation based on the three datasets with different echo times.
Processing and Display
  a. Display as a 3D volume (set of 2D slices, see FIG. 2 as included in the Provisional Application to which this application claims the benefit).

EXEMPLARY APPLICATIONS

1. Characterization of 3D cardiac wall motion in its natural physiologic state with respect to cardiac and/or respiratory motion.
2. Characterization of 3D cardiac volumes and the variations with respect to cardiac and/or respiratory motion.
3. Characterization of functional information, such as flow and perfusion, and correlate the results with the underlying 3D morphology and physiologic motion.

4. Characterization of the distribution of a contrast agent and correlate the results with the underlying 3D morphology and physiologic motion (e.g., time-resolved volumetric imaging of myocardial scarring or general tumor physiology).

5. Observation of changes in the state of the heart over time or when under different conditions.

Embodiments of the invention have several advantages of prior solutions and techniques. For example:

1. Rapid acquisition of multiple-dimensions of information effectively resolves the sources of physiologic motion and avoids artifacts arising from such motion.

2. Anatomic and physiologic information are co-registered.

3. The heart can be observed in its natural physiologic state.

4. Ease of use. No respiratory cooperation is expected from the patient.

5. Ease of prescription. Can prescribe coverage over whole heart with isotropic resolution.

6. The comprehensive multi-dimensional acquisition allows for flexible repeated inspection of a plurality of information retrospectively.

Embodiments of the invention can be varied. For example:

1. The imaging modality can be different from MRI and use different contrast mechanisms, such as 3D X-ray computed tomography (CT) or 3D echocardiography.

2. Additional functional information can be acquired in the multi-dimensional acquisition (see also point 10 and 11).

3. Imaging contrast agents can be administered.

4. The imaging region of interest can be extended beyond the heart.

5. The imaging subject can also be non-human.

6. This 5D MRI technique can be performed with induced respiratory pressure variations, such as by using a respiratory mask connected to a continuous positive airway pressure (CPAP) device, to study the cardiac pressure-volume relationship in different disease states (including diastolic dysfunction).

7. The implementation can be based on other imaging sequences besides SSFP, such as spin echo, fast spin echo, gradient echo, or radio-frequency-spoiled gradient echo.

8. The volumetric reconstruction can employ a non-uniform fast Fourier transform instead of 3D re-gridding and a regular Fourier transform.

9. Additional acceleration can be achieved by parallel imaging reconstruction, constrained spatiotemporal reconstruction, or compressed sensing reconstruction.

10. This 5D MRI technique can be augmented to acquire additional dimensions of information, such as perfusion or flow.

11. MRI has a distinct advantage in offering multiple contrast mechanisms for obtaining anatomic and functional information (including T1 weighting, T2 weighting, proton-density weighting, flow, oxygenation level, diffusion, chemical shift, the distribution of an imaging agent, etc.), which can all be considered in this invention to provide a multi-dimensional view of the human heart or other regions of interest.

CONCLUSION

The embodiments of the invention advances the art in at least the following aspects:

1. Explicit characterization of the human heart and other regions of interest in a multi-dimensional anatomic and physiologic state and capturing the state with a rapid acquisition technique.

2. Explicitly resolving sources of physiologic motion that can otherwise lead to artifacts.

3. Deriving quantitative measurements from the multi-dimensional data and to correlating it to other dimensions of information.

4. Integrated visualization of multiple dimensions of information to facilitate the diagnosis of the condition of the human heart and other regions of interest.

More specifically, the embodiments of the invention advances the art in at least the following aspects:

1. A fast multi-dimensional magnetic resonance imaging (MRI) procedure which records and correlates at least five dimensions of anatomic, physiologic, and functional information, either spontaneous or induced, exclusive of common ECG triggering to diagnose cardiovascular conditions.

The mechanisms of generating MR image contrast for this procedure include (but is not limited to) T1 weighting, T2 weighting, proton-density weighting, flow, oxygenation level, diffusion, chemical shift, and the distribution of an imaging agent.

2. Post-processing of the acquired multi-dimensional data to derive quantitative measurements and functional information governed by variables other than traditional cardiac gating. For example, dynamic volume measurements obtained from the anatomic data, dynamic changes in cardiac ejection fraction, perfusion, flow, and changes in cardiac rhythm.

3. Representation and visualization of the raw acquired multi-dimensional data and derived measurements. (e.g. Variations in volume measurements of the anatomy correlated to changes in respiratory and cardiac motion).

4. Observations and tests made possible to facilitate diagnosis of cardiovascular conditions.

5. Evaluation of cardiac systolic and diastolic performance during ventricular or atrial arrhythmia.

6. Evaluation of cardiac systolic and diastolic performance during coached respiration.

7. Evaluation of cardiac systolic and diastolic performance during restricted respiration such as during positive-pressure respiration.

8. Evaluation of cardiac systolic and diastolic performance with respect to changes in venous flow.

9. Evaluation of cardiac systolic and diastolic performance with respect to changes in the oxygenation level of the blood pool and/or myocardium.

10. A time-resolved multi-dimensional MRI procedure utilizing a fast 3D readout trajectory, including, but not limited to, the 3D cones, 3D Periodically Rotated Overlapping ParallEL Lines with Enhanced Reconstruction (PROPELLER), 3D projection reconstruction (PR), and 3D echo-planar imaging (EPI), for spatial encoding, thereby realizing rapid acquisition of volumetric anatomical information along with physiologic and functional information.

11. A time-resolved multi-dimensional T1-weighted MRI procedure utilizing a centric-ordered readout trajectory, including, but not limited to, the 3D stack-of-rings and 3D cylinders, for spatial encoding and magnetization-preparation modules for contrast generation to realize rapid acquisition of volumetric anatomical information along with physiologic and functional information.

12. Time-resolved volumetric representation of contrast uptake for perfusion and delayed-enhancement imaging (e.g. to visualize perfusion defects and/or myocardial scarring).

13. Time-resolved volumetric representation of tissue T1 values.

14. A time-resolved multi-dimensional T2-weighted MRI procedure utilizing a fast 3D readout trajectory, including, but not limited to, the 3D cones and the 3D stack-of-rings, in a magnetization-prepared gradient-echo or fast-spin-echo imaging sequence for rapid acquisition of volumetric anatomical information along with physiologic and functional information.

15. Time-resolved volumetric representation of tissue T2 values.

16. Complementing the 3-dimensional spatial information with MRI acceleration techniques, such as parallel imaging, compressed sensing, spatiotemporal undersampling and reconstruction.

17. Multi-dimensional acquisition with additional flow or perfusion encoding.

18. Conjunction with induced respiratory pressure variations, such as using a continuous positive airway pressure (CPAP) device.

Examples of the present invention could be embodied in various ways, for example, but not limited to the use of computer systems, software programs or modules executable on computers as well as electronically programmed or design chip or boards. The embodiments could be used in conjunction with imaging systems or devices, data acquisition or recording devices or the like.

What is claimed is:

1. A 5-dimensional magnetic resonance (MR) imaging method of a patient's heart, comprising:
   (a) in a patient free-breathing magnetic resonance imaging study of said patient's heart, a magnetic resonance imaging (MRI) computer system acquiring 3-dimensional volumetric spatial information of said patient's heart and concurrently recording cardiac and respiratory cycles of said patient, wherein said 3-dimensional volumetric spatial information is sampled with a non-Cartesian 3-dimensional k-space readout trajectory which is incorporated into a magnetic resonance imaging sequence, wherein said MRI computer system acquisition comprises a plurality of MRI acquisition segments of a plurality of readouts of said heart, whereby each segment is repeated multiple times in order to cover the at least a full period of a cardiac cycle and at least a full period of a respiratory cycle of said patient, wherein the MRI computer system combines the acquired 3-dimensional volumetric spatial information of the non-Cartesian 3-dimensional K-space readout trajectory in the MRI sequence with the plurality of readouts of the heart representing said at least full period of the cardiac cycle and said at least full period respiratory cycle, whereby the plurality of readouts of said heart for both the cardiac and respiratory cycles are defined as 2-dimensional non-spatial information in order to form a 5-dimensional data map of the patient's heart; and
   (b) for each cardiac and respiratory temporal phase combination in said recorded cycles, said MRI computer system displaying at least one of the 3-dimensional volumetric spatial measurements of the atria and ventricles of said patient's heart, together with either the rate of change, minimum, maximum, or slope of these volume based measurements with respect to each of said cardiac and respiratory cycles, wherein the MRI system computer displays 3 of the 5 dimensions that are selected from the 5-dimensional data map, and wherein at least one non-spatial dimension is displayed as one of the 3 dimensions selected from the 5-dimensional data map that is displayed.

2. The method as set forth in claim 1, wherein said non-Cartesian 3-dimensional k-space readout trajectory is selected as either: a non-Cartesian 3-dimensional cones k-space readout trajectory, a non-Cartesian 3-dimensional echo-planar imaging (EPI) k-space readout trajectory, a non-Cartesian 3D Periodically Rotated Overlapping ParallEL Lines with Enhanced Reconstruction (PROPELLER) k-space readout trajectory, a non-Cartesian 3D stack of spirals k-space readout trajectory, a non-Cartesian 3D stack of rings k-space readout trajectory, or a non-Cartesian 3-dimensional projection reconstruction (PR) k-space readout trajectory, or any other rapid 3D k-space readout trajectory.

3. The method as set forth in claim 1, wherein said non-Cartesian 3-dimensional k-space readout trajectory traverses data points along arbitrary trajectories instead of the straight rectilinear line trajectories that are common in Cartesian sampling.

4. The method as set forth in claim 1, wherein said non-Cartesian 3-dimensional k-space readout trajectory traverses data points occurring along intersecting diagonal line trajectories, spiraling trajectories, circular trajectories occurring within a 3D k-space, or a combination thereof.

5. The method as set forth in claim 1, complementing the acquisition of said 3-dimensional volumetric spatial information with MRI acceleration techniques of parallel imaging, spatiotemporal undersampling and reconstruction, compressed sensing or a combination thereof.

6. The method as set forth in claim 1, wherein said magnetic resonance imaging sequence utilizes principles of free-induction decay, steady-state free precession, gradient echo, spin echo, magnetization preparation modules, or a combination thereof in order to prepare image contrast from the magnetically resonant spins.

7. The method as set forth in claim 1, wherein the respiratory and cardiac cycles are recorded by using at least one of: an electrocardiogram (ECG), pulse-ox plethysmograph, respiratory bellows, MRI navigators, MRI self-navigation signals, auxiliary ultrasound information, auxiliary optical sensors, or a combination thereof.

8. The method as set forth in claim 1, complementing said 3-dimensional volumetric spatial information, respiratory information, and cardiac information with additional flow information, perfusion information or a combination thereof.

9. The method as set forth in claim 1, complementing said 3-dimensional volumetric spatial information and respiratory and cardiac information with MRI T1-relaxation information, MRI T2-relaxation information, or a combination thereof.

10. The method as set forth in claim 1, complementing said 3-dimensional volumetric spatial information and respiratory and cardiac information with oxygenation level information, the distribution of an administered contrast agent or a combination thereof.

11. The method as set forth in claim 1, complementing said 3-dimensional volumetric spatial information and respiratory and cardiac information with diffusion information.

12. The method as set forth in claim 1, complementing said 3-dimensional volumetric spatial information and respiratory and cardiac information with MR resonant frequency information.

13. The method as set forth in claim 1, said patient free-breathing magnetic resonance imaging study further comprising internally or externally inducing respiratory pressure variations to said patient with a respiratory bellows.

* * * * *

UNITED STATES PATENT AND TRADEMARK OFFICE
CERTIFICATE OF CORRECTION

| | | |
|---|---|---|
| PATENT NO. | : 9,121,915 B2 | Page 1 of 1 |
| APPLICATION NO. | : 13/374045 | |
| DATED | : September 1, 2015 | |
| INVENTOR(S) | : Wu et al. | |

It is certified that error appears in the above-identified patent and that said Letters Patent is hereby corrected as shown below:

In the specification

Column 1, line 11 delete

"STATEMENT OF GOVERNMENT SPONSORED SUPPORT
This invention was made with Government support under contracts R01-HL039297 and NIH/NIBIB T32-EB009035 awarded by National Institutes of Health (NIH). The Government has certain rights in this invention."

insert

--STATEMENT OF GOVERNMENT SPONSORED SUPPORT
This invention was made with Government support under contracts EB009305 and HL039297 awarded by the National Institutes of Health. The Government has certain rights in the invention.--

Signed and Sealed this
Twelfth Day of April, 2016

Michelle K. Lee
*Director of the United States Patent and Trademark Office*